US008481439B2

(12) United States Patent
Yamashita et al.

(10) Patent No.: US 8,481,439 B2
(45) Date of Patent: Jul. 9, 2013

(54) COLORED ALUMINA SINTERED BODY OF HIGH TOUGHNESS AND HIGH TRANSLUCENCY, AND ITS PRODUCTION METHOD AND ITS USES

(75) Inventors: Isao Yamashita, Kanagawa (JP); Koji Tsukuma, Kanagawa (JP)

(73) Assignee: Tosoh Corporation, Tokyo (JP)

( * ) Notice: Subject to any disclaimer, the term of this patent is extended or adjusted under 35 U.S.C. 154(b) by 0 days.

(21) Appl. No.: 13/121,884

(22) PCT Filed: Nov. 13, 2009

(86) PCT No.: PCT/JP2009/069393
§ 371 (c)(1),
(2), (4) Date: Mar. 30, 2011

(87) PCT Pub. No.: WO2010/058745
PCT Pub. Date: May 27, 2010

(65) Prior Publication Data
US 2011/0189622 A1 Aug. 4, 2011

(30) Foreign Application Priority Data
Nov. 18, 2008 (JP) .................. 2008-294498
Nov. 18, 2008 (JP) .................. 2008-294499

(51) Int. Cl.
*C04B 35/115* (2006.01)
(52) U.S. Cl.
USPC ............. 501/127; 501/128; 501/153; 433/8
(58) Field of Classification Search
USPC .................. 501/127, 128, 153; 433/8
See application file for complete search history.

(56) References Cited

U.S. PATENT DOCUMENTS
3,026,210 A 3/1962 Coble
4,889,834 A 12/1989 Niihara et al.
(Continued)

FOREIGN PATENT DOCUMENTS
JP 59-169979 A 9/1984
JP 63-239154 A 10/1988
(Continued)

OTHER PUBLICATIONS
Claussen, Nils. "Fracture toughness of Al2O3 with an Unstabilized ZrO2 Dispersed Phase"; Journal of the American Ceramic Society, vol. 59, No. 1-2, pp. 49-51. 1976.
(Continued)

*Primary Examiner* — Karl Group
(74) *Attorney, Agent, or Firm* — Westerman, Hattori, Daniels & Adrian, LLP

(57) ABSTRACT

Because fracture toughness and translucency of translucent colored alumina sintered body of the past were low, the alumina sintered body was not suitable for uses such as dental materials, which require high toughness. The present invention relates to providing a translucent colored alumina sintered body that contains transition metal oxides, and with which the fracture toughness is 4.5 MPa·m$^{0.5}$ or more and the maximum value of total forward transmittance (sample thickness 1 mm) to a wavelength of 300-800 nm is 60% or more. The present invention relates to obtaining a sintered body, at least 20% of which contains anisotropic grains with a long axis length of 10 μm or greater and an aspect ratio of 1.5 or more by subjecting an alumina sintered body containing transition metal oxides having a eutectic point with alumina or an alumina sintered body containing transitional metal oxides and at least one selected from the group consisting of Group 1A alkali metal oxides, Group 2A alkaline earth metal oxides, and $SiO_2$, $B_2O_3$, $P_2O_5$ and $GeO_2$ to pressureless sintering and HIP treatment.

15 Claims, 3 Drawing Sheets

SAMPLE NO. 1-1

U.S. PATENT DOCUMENTS

| | | | | |
|---|---|---|---|---|
| 5,256,611 | A | * | 10/1993 | Moltgen et al. ............... 501/127 |
| 5,625,256 | A | * | 4/1997 | Tiedt et al. .................... 313/636 |
| 6,143,678 | A | | 11/2000 | Yamamoto et al. |
| 6,194,336 | B1 | | 2/2001 | Yoshizawa et al. |
| 6,383,963 | B1 | | 5/2002 | Yamamoto et al. |
| 6,417,127 | B1 | | 7/2002 | Yamamoto et al. |
| 7,456,122 | B2 | * | 11/2008 | Rhodes et al. ................ 501/153 |
| 7,888,279 | B2 | | 2/2011 | Tsukuma et al. |
| 2006/0169951 | A1 | | 8/2006 | Van Bruggen et al. |
| 2007/0027026 | A1 | * | 2/2007 | Rhodes et al. ................ 501/153 |
| 2007/0278960 | A1 | | 12/2007 | Van Bruggen et al. |
| 2009/0111067 | A1 | | 4/2009 | Tsukuma et al. |
| 2009/0137380 | A1 | * | 5/2009 | Bernard-Granger et al. . 501/125 |
| 2011/0027742 | A1 | * | 2/2011 | Fujisaki et al. .................... 433/8 |

FOREIGN PATENT DOCUMENTS

| | | | |
|---|---|---|---|
| JP | 64-87552 | A | 3/1989 |
| JP | 1-133973 | A | 5/1989 |
| JP | 2-255563 | A | 10/1990 |
| JP | 3-261648 | A | 11/1991 |
| JP | 4-193760 | A | 7/1992 |
| JP | 9-87008 | A | 3/1997 |
| JP | 11-001365 | A | 1/1999 |
| JP | 2000-53463 | A | 2/2000 |
| JP | 2001-322866 | A | 11/2001 |
| JP | 2002-012471 | A | 1/2002 |
| JP | 2002-293613 | A | 10/2002 |
| JP | 2004-204912 | A | 7/2004 |
| JP | 2007182348 | * | 7/2007 |
| JP | 2008-195581 | A | 8/2008 |
| JP | 2009-107887 | A | 5/2009 |

OTHER PUBLICATIONS

Isao, Yamashita and Koji, Tsukuma. "Translucent Al2O3/LaAl11O18 Composite"; Journal of the American Ceramic Society, vol. 92, No. 9, pp. 2136-2138. Oct. 14, 2009, (received date).

International Search Report of PCT/JP2009/069393, date of mailing Feb. 2, 2010.

Extended European Search Report dated Mar. 26, 2013, issued in corresponding European Patent Application No. 09827526.6 (12 pages).

Bernard-Granger et al., "Influence of MgO or TiO2 doping on the sintering path and on the optical properties of a submicronic alumina material", Scripta Materialia, Elsevier, Amsterdam, NL, vol. 56, No. 11, Apr. 6, 2007, pp. 983-986, XP022024008. (Cited in EESR dated Mar. 26, 2013).

Nagashima et al., "Fabrication and optical characterization of high-density Al2O3 doped with slight MnO dopant", Journal of the Ceramic Society of Japan, vol. 116, No. 1353, Jan. 1, 2008, pp. 645-648, XP055056844. (Cited in EESR dated Mar. 26, 2013).

Taimei Chemicals Co. et al., "High purity alumina "Taimicron" ", Jan. 1, 2008, XP055056900; 4 ppges. (Cited in EESR dated Mar. 26, 2013).

* cited by examiner

SAMPLE NO. 1-1

SAMPLE NO. 2-1

SAMPLE NO. 3-1

COLORED ALUMINA SINTERED BODY OF HIGH TOUGHNESS AND HIGH TRANSLUCENCY, AND ITS PRODUCTION METHOD AND ITS USES

TECHNICAL FIELD

The present invention relates to a colored alumina sintered body having both high toughness and excellent translucency, which is not only useful in ornament, jewelry and craftwork articles, but available as dental materials such as an orthodontic bracket and a mill blank for artificial denture which require high value in toughness.

BACKGROUND ART

Recently, a translucent alumina sintered body has been widely utilized not only in ornament, jewelry and craftwork articles, but as dental materials such as an orthodontic bracket and a mill blank for artificial denture. As its use is extended to such dental materials, the improvement of mechanical properties such as fracture toughness in addition to aesthetic nature based on translucency become an important issue in the translucent alumina sintered body. In particular, since a need for a translucent ceramic bracket characterized by coloring is increased recently, the enhancement in toughness of a translucent alumina sintered body characterized by coloring (hereinafter, translucent colored alumina sintered body) is desired.

Conventionally, as artificial jewelry such as ruby and sapphire, a translucent colored alumina has been produced by Verneuil method, Czochralski method or the like. However, since monocrystals are obtained in such methods, work for a machining of such monocrystals in practical use is required.

To decrease work due to the machining, a method of mixing an alumina powder with transition metal oxides such as chromium oxide, cobalt oxide, and iron oxide, and molding/sintering the mixed powder had been invented (Patent documents 1-6). For example, Patent document 1 discloses a method of mixing an alumina powder with cobalt oxide, nickel oxide, chromium oxide, manganese oxide, and so on, and sintering the mixture under hydrogen or vacuum atmosphere. Furthermore, Patent document 2 discloses a method for producing a translucent colored alumina sintered body by a hot isostatic pressing (HIP) using transition metals such as iron oxide, titanium oxide, vanadium oxide, nickel oxide, chromium oxide and cobalt oxide. Using these methods, translucent colored alumina sintered bodies having color such as blue, green, yellow and pink are obtained.

However, to date, methods for producing a translucent colored alumina sintered body were based on production methods under hydrogen or vacuum atmosphere (for example, Patent document 7), or methods using HIP (for example, Patent document 8), and translucent colored alumina sintered bodies produced by these methods had fracture toughness as low as 3-4 MPa·m$^{0.5}$ (Patent document 8). Therefore, high value in fracture toughness suitable for uses which require mechanical properties was not obtained.

Regarding the enhancement in toughness of an alumina sintered body, there are reports such as the introduction of different phases (Patent document 9, and Non-Patent document 1) and the anisotropic grain growth of alumina grains (Patent documents 10 and 11). Using these methods, high value in fracture toughness is obtained, but translucency does not appear. The reason for this is considered that the introduction of different phases causes light scattering at interfaces of different phases, and also a sintered body texture containing anisotropic grains, which can be formed by said conventional method, lowers translucency (Patent document 12).

Thus, to date, a translucent colored alumina sintered body having both high fracture toughness and translucency has not been obtained.

PRIOR-ART DOCUMENTS

Patent Documents

Patent document 1: JP-A-59-169979 bulletin
Patent document 2: JP-A-63-239154 bulletin
Patent document 3: JP-A-1-133973 bulletin
Patent document 4: JP-A-4-193760 bulletin
Patent document 5: JP-A-2002-12471 bulletin
Patent document 6: JP-A-2002-293613 bulletin
Patent document 7: U.S. Pat. No. 3,026,210 specification
Patent document 8: JP-A-3-261648 bulletin
Patent document 9: JP-A-64-87552 bulletin
Patent document 10: JP-A-11-1365 bulletin
Patent document 11: JP-A-9-87008 bulletin
Patent document 12: JP-A-2001-322866 bulletin

Non-Patent Document

Non-Patent document 1: American Ceramic Society Bulletin, Vol. 59, Page 49 (1976)

SUMMARY OF THE INVENTION

Problems that the Invention is to Solve

The present invention relates to providing a colored alumina sintered body having both high toughness and translucency, and a method for producing the same.

Means for Solving the Problems

As a result of earnest studies on the improvement of coloring, translucency and fracture toughness of an alumina sintered body, the inventors of the present invention have found that a sintered body having coloring with excellent aesthetic nature, excellent translucency and high fracture toughness is obtained by achieving a sintered grain texture having anisotropic grains using transition metal oxides, and have reached to complete the present invention.

That is, the gist of the present invention resides in the following (1)-(16).
(1) An alumina sintered, characterized in that the alumina sintered body contains transition metal oxides, the fracture toughness is 4.5 MPa·m$^{0.5}$ or more, and the maximum value of total forward transmittance of a sample having a thickness of 1 mm to a light having a wavelength of 300-800 nm is 60% or more.
(2) The alumina sintered body as described in (1), wherein preferably the transition metal oxide contains in the range of 100 ppm-3 wt % in total.
(3) The alumina sintered body as described in (1) or (2), wherein preferably sintered grains comprise anisotropic grains having a long axis length of 10 μm or greater, and an aspect ratio of 1.5 or more.
(4) The alumina sintered body as described in (3), wherein preferably the fraction of anisotropic grains having a long axis length of 10 μm or greater, and an aspect ratio of 1.5 or more is 20 vol % or more.
(5) The alumina sintered body as described in any one of (1) to (4), wherein preferably the transition metal oxide has a eutectic point with alumina.
(6) The alumina sintered body as described in (5), wherein preferably the transition metal oxide having a eutectic point with alumina is at least one selected from the group consisting of manganese oxide, copper oxide, vanadium oxide, iron oxide, titanium oxide, and nickel oxide.

(7) The alumina sintered body as described in any one of (1) to (6), preferably further containing at least one selected from the group consisting of Group 1A alkali metal oxides, Group 2A alkaline earth metal oxides, and $SiO_2$, $B_2O_3$, $P_2O_5$ and $GeO_2$.

(8) The alumina sintered body as described in (7), preferably containing at least one selected from the group consisting of Group 1A alkali metal oxides, Group 2A alkaline earth metal oxides, and $SiO_2$, $B_2O_3$, $P_2O_5$ and $GeO_2$ in the range of 20-1000 ppm.

(9) A method for producing an alumina sintered body, characterized by molding an alumina powder containing transition metal oxides in the range of 100 ppm-3 wt % in total, pressureless sintering the resulting molded article, and subjecting the resulting sintered body to a hot isostatic pressing (HIP) treatment.

(10) The method for producing an alumina sintered body as described in (9), wherein preferably the transition metal oxide is at least one selected from the group consisting of manganese oxide, copper oxide, vanadium oxide, iron oxide, titanium oxide, and nickel oxide.

(11) The method for producing an alumina sintered body as described in (9) or (10), wherein preferably the alumina powder further contains at least one selected from the group consisting of Group 1A alkali metal oxides, Group 2A alkaline earth metal oxides, and $SiO_2$, $B_2O_3$, $P_2O_5$ and $GeO_2$ in the range of 20-1000 ppm in total.

(12) The production method as described in any one of (9) to (11), characterized by preferably using a high purity alumina powder having a specific surface area of 5-20 m²/g, and the fraction of 1 μm or smaller fine grains of 90 vol % or more.

(13) The production method as described in any one of (9) to (12), wherein preferably the pressureless sintering is conducted at a temperature of 1250-1450° C.

(14) The production method as described in any one of (9) to (13), wherein preferably the hot isostatic pressing (HIP) treatment is conducted at a temperature of 1350-1750° C. under a pressure of 50 MPa or more.

(15) A dental material, characterized by using the alumina sintered body as described in any one of (1) to (8).

(16) The dental material as described in (15), which is preferably an orthodontic bracket or a mill blank for artificial denture.

Advantages of the Invention

A conventional translucent colored alumina sintered body had low toughness, destroyed during processing, and lacked impact-resistance when applying stress. The alumina sintered body of the present invention has coloring with high aesthetic nature and translucency, as well as higher toughness than that of the conventional sintered body, and thus it has excellent processability, and does not destroy or break.

MODES FOR CARRYING OUT THE INVENTION

Figure 1:
FIG. 1 is a view showing the sintered body texture (Sample No. 1-1) of the present invention (scale in Figure=20 μm).
Figure 2:
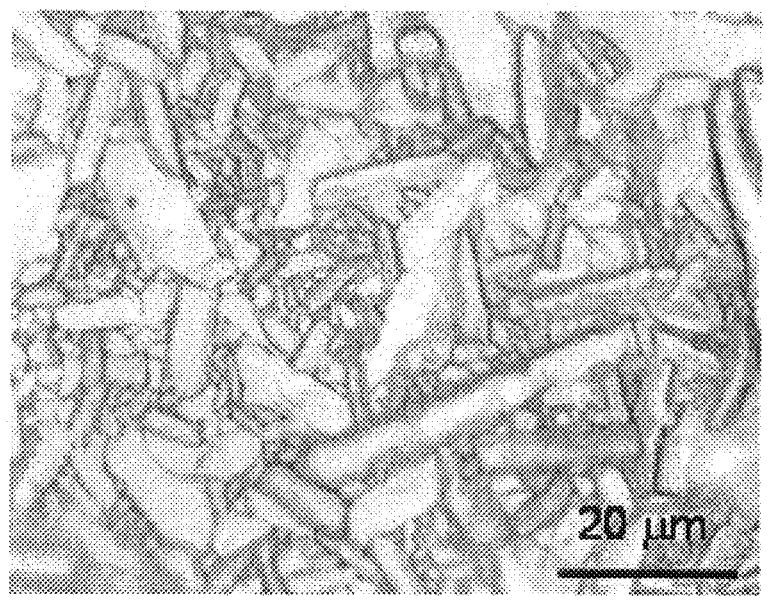
FIG. 2 is a view showing the sintered body texture (Sample No. 2-1) of the present invention (scale in Figure=20 μm).
Figure 3:
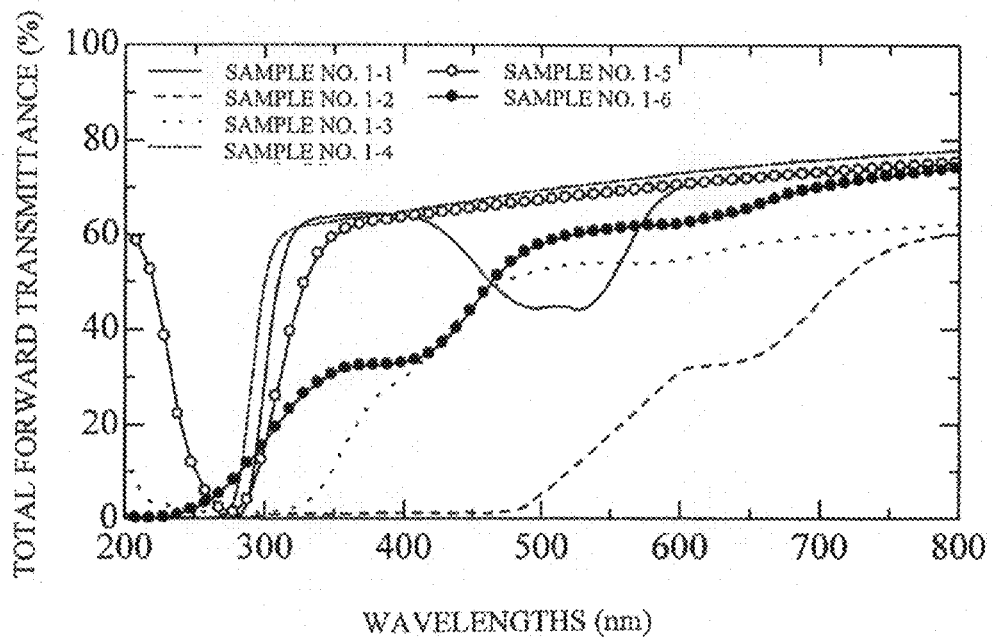
FIG. 3 shows total forward transmittance of the sintered body of Example 1 (sample thickness 1 mm).
Figure 4:
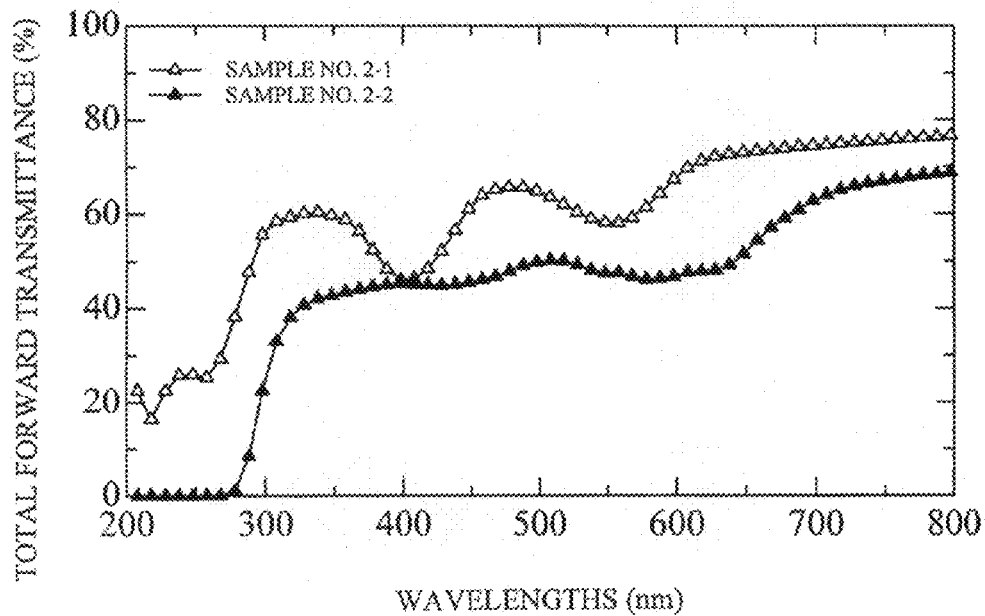
FIG. 4 shows total forward transmittance of the sintered body of Example 2 (sample thickness 1 mm).
Figure 5:
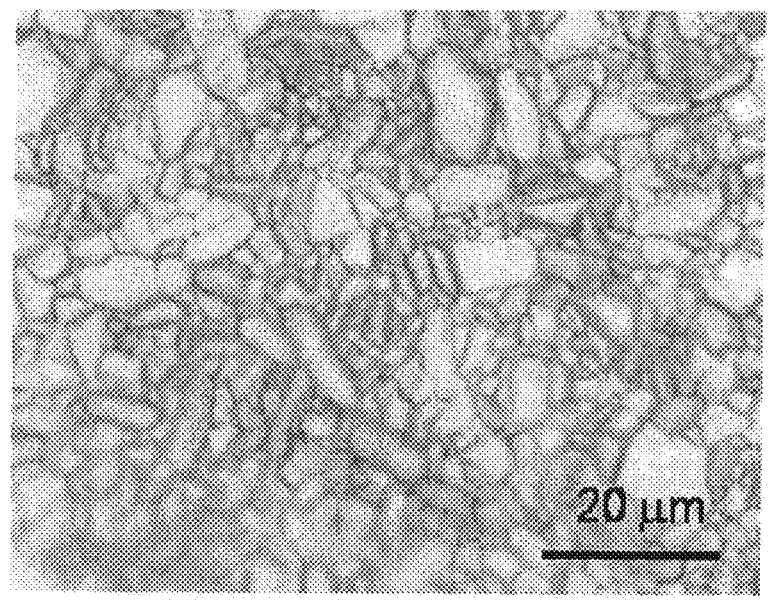
FIG. 5 is a view showing the sintered body texture (Comparative Example 1, Sample No. 3-1) of the Comparative Example (scale in Figure=20 μm).

An alumina sintered body of the present invention is described below.

An alumina sintered body of the present invention contains transition metal oxides. Thus, a transparent alumina sintered body having the intended color can be obtained.

In the present invention, a content of the transition metal oxide is preferably 100 ppm-3 wt %, and particularly preferably 300 ppm-1 wt %. If the content is less than 100 ppm, an effect of adding the transition metal oxide is liable to be poor, and if the content exceeds 3 wt %, the transition metal oxide in alumina reaches a limit of solid solution, and consequently grains of transition metal oxide are precipitated in the sintered body, and translucency is liable to be lowered.

In the sintered body of the present invention, fracture toughness is 4.5 MPa·m$^{0.5}$ or more, particularly preferably 5 MPa·m$^{0.5}$ or more, and more preferably 6 MPa·m$^{0.5}$ or more.

The sintered body of the present invention has high translucency, wherein the maximum value of total forward transmittance of a sample having a thickness of 1 mm to a light having a wavelength of 300-800 nm is 60% or more, 65% or more, particularly preferably 70% or more, and more preferably 75% or more.

In the sintered body of the present invention, flexural strength is not particularly limited, but it is preferably 350 MPa or more, particularly preferably 400 MPa or more, and more preferably 500 MPa or more.

Methods for evaluating fracture toughness and flexural strength herein are based on methods defined in JIS, and all values in the present invention are average values (average fracture toughness and average flexural strength).

Preferably, the alumina sintered body of the present invention contains anisotropic grains having a long axis length of 10 μm or greater and an aspect ratio of 1.5 or more as sintered grains. In particular, the aspect ratio of anisotropic grains is preferably 3 or more. The greater the aspect ratio of anisotropec grains, the higher the fracture toughness. A representative example of alumina sintered grains constituting the alumina sintered body of the present invention is shown in FIG. 1.

A content of anisotropic grains in the alumina sintered body of the present invention is preferably 20 vol % or more, particularly preferably 30 vol %, and more preferably 50 vol % or more. The more the content of anisotropic grains increases, the more the fracture toughness of sintered body increases. Meanwhile, as the content of anisotropic grains approach 100 vol %, the fracture toughness becomes 10 MPa·m$^{0.5}$ or more, but the flexural strength is liable to be lowered up to 300 MPa. Therefore, the content of anisotropic grains does not need to increase excessively.

It is preferred that anisotropic grains in the alumina sintered body of the present invention are particularly plate-shaped grains (anisotropic plate-shaped grains).

A sintered texture of the alumina sintered body of the present invention comprises equi-axis grains in addition to anisotropic grains, and anisotropic grains contribute to the enhancement of fracture toughness, while equi-axis grains help to interconnect anisotropic grains to contribute to the maintenance of strength.

The alumina sintered body of the present invention has high toughness and translucency by virtue of the sintered texture containing specific anisotropic grains, and is different from conventional sintered bodies having low toughness containing aids such as magnesium oxide.

The transition metal oxide contained in an alumina sintered body of the present invention is preferably transition metal oxides having a eutectic point with alumina, and particularly preferably at least one selected from the group consisting of manganese oxide, copper oxide, vanadium oxide, iron oxide, titanium oxide, and nickel oxide. These transition metal oxides not only impart the intended color, but also provide liquid phase in alumina, resulting in promoting anisotropic grain growth of alumina grains.

Preferably, the alumina sintered body of the present invention contains additionally at least one selected from the group consisting of Group 1A alkali metal oxides, Group 2A alkaline earth metal oxides, and $SiO_2$, $B_2O_3$, $P_2O_5$ and $GeO_2$ in the range of 20-1000 ppm in total, in addition to the transition metal oxide. Group 1A alkali metal oxides such as $Na_2O$, Group 2A alkaline earth metal oxides, and $SiO_2$, $B_2O_3$, $P_2O_5$ and $GeO_2$ act as a glass forming aid to promote anisotropic grain growth of alumina grains. The oxides having high glass-forming ability are particularly $Na_2O$, and $Na_2O+SiO_2$. Herein, examples of Group 1A alkali metals of Periodic Table include lithium, sodium, potassium, rubidium and cesium.

Meanwhile, MgO belongs to Group 2A alkaline earth metal oxides, but MgO shows an effect of acting as a grain growth inhibitor. Therefore, when MgO is used as Group 2A alkaline earth metal oxides, one or more components from the group consisting of Group 1A alkali metal oxides, $SiO_2$, $B_2O_3$, $P_2O_5$, $GeO_2$ and Group 2A alkaline earth metal oxides other than MgO must be added additionally. Therefore, it is preferred that Group 2A alkaline earth metal oxides other than MgO are used. Herein, examples of Group 2A alkaline earth metals of Periodic Table include beryllium, magnesium, calcium, strontium and barium.

A content of one or more components selected additionally from the group consisting of Group 1A alkali metal oxides, $SiO_2$, $B_2O_3$, $P_2O_5$, $GeO_2$ and Group 2A alkaline earth metal oxides other than MgO contained in the alumina sintered body of the present invention is preferably 20-1000 ppm in total. If the content is less than 20 ppm, an effect of adding it may be poor, and if the content exceeds 1000 ppm, sintering may be inhibited.

In addition, rare earth metal oxides such as erbium oxide and europium oxide have an effect of coloring an alumina sintered body. However, it is not preferable to use such oxides, since they inhibit sintering and lower translucency and fracture toughness.

When the alumina sintered body of the present invention contains at least one selected from the group consisting of Group 1A alkali metal oxides, Group 2A alkaline earth metal oxides, and $SiO_2$, $B_2O_3$, $P_2O_5$ and $GeO_2$ in the range of 20-1000 ppm in total, the transition metal oxide used is not particularly limited so long as the intended color is colored. For example, cobalt oxide appearing blue, chromium oxide appearing red and the like may be used.

Subsequently, a method for producing an alumina sintered body of the present invention is described.

A sintered body of the present invention can be produced by molding an alumina powder containing transition metal oxides in the range of 100 ppm-3 wt % in total, pressureless sintering the resulting molded article, and subjecting the resulting sintered body to a hot isostatic pressing (HIP) treatment.

The transition metal oxide is preferably transition metal oxides having a eutectic point with alumina, and particularly preferably at least one selected from the group consisting of manganese oxide, copper oxide, vanadium oxide, iron oxide, titanium oxide, and nickel oxide.

Preferably, the alumina powder contains additionally at least one selected from the group consisting of Group 1A alkali metal oxides, Group 2A alkaline earth metal oxides, and $SiO_2$, $B_2O_3$, $P_2O_5$ and $GeO_2$ in the range of 20-1000 ppm in total, in addition to the transition metal oxide. These oxides promote anisotropic grain growth of alumina grains. For this reason, when containing such oxides, the type of transition metal oxide contained in the alumina powder is not limited, any transition metal oxide appearing the intended color may be used.

In the production method of the present invention, the alumina powder as a raw material in which said different types of components are added is a high purity alumina powder having purity of 99.99% or more, and it is preferred that the alumina powder includes fine grains having a specific surface area of 5-20 $m^2/g$, wherein the fraction of 1 μm or smaller fine grains is 90 vol % or more. By using the high purity alumina powder as a starting raw material, a content of different types of components become uniform, resulting in obtaining a high quality sintered body. The fraction of fine grains in the alumina powder is important, and it is not preferred that the fraction of fine grains is less than 90%, since a temperature for achieving densification by sintering is raised in such a case.

In the production method of the present invention, said different types of components are added in the alumina powder, and the mixture may be preferably dispersed by a mixing and/or grinding apparatus. A method for mixing and/or grinding the mixture may be a wet method using water, ethanol and the like, or a dry method.

Said different types of oxides may be added as oxide powders, or precursors (chlorides, inorganic acid salts, organic acid salts and the like) which become oxides by a firing process. Furthermore, in case of alkali metal oxides, water-soluble salts such as NaCl may be used. These raw materials are mixed so as to satisfy predetermined amounts, and the resulting mixture may be dried and/or sintered.

In the production method of the present invention, a method for molding the powder is not particularly limited, and various methods such as mold press, rubber press, slip casting, and injection molding may be applied, for example.

In the production method of the present invention, after pressureless sintering of a molded body of alumina powder having said composition, a hot isostatic pressing (HIP) treatment is conducted.

In the production method of the present invention, it is preferred that pressureless sintering is conducted at a temperature of 1250-1450° C. under the atmosphere of air, oxygen, vacuum or the like. The pressureless sintering densifies a sintered body to density (about 95% of theoretical density) required for subsequent HIP treatment. If the density after pressureless sintering is less than 95% of theoretical density, pores cannot be removed by the penetration of a pressure medium gas for HIP treatment within the sintered body.

It is preferred in pressureless sintering that residual pores within the sintered body have a form which can be removed effectively by HIP treatment, and particularly intergranular pores may be easily removed relative to intragranular pores. Therefore, if the sintering temperature of pressureless sintering is too high, the phenomenon that pores enter grains by grain growth may be easily generated, and it is difficult to remove such pores by HIP treatment. Furthermore, the more the crystalline grains of a primary sintered body applied to HIP treatment is fine, the more the translucency of sintered body after HIP treatment is increased. Thus, from standpoints of obtaining 95% or more of theoretical density, inhibiting the generation of intragranular pores, and obtaining fine crystalline grains, pressureless sintering is preferably conducted at a temperature of 1250-1450° C.

In the production method of the present invention, HIP treatment is conducted to remove residual pores within a sintered body and impart translucency thereto. It is preferred that a treatment temperature is 1200° C. or more, and a treatment pressure is 50 MPa or more. In particular, a temperature of 1300-1800° C. and a pressure of 100-200 MPa is preferable. If the temperature is less than 1200° C., the growth of anisotropic grains is insufficient, and if the temperature exceeds 1800° C., anisotropic grains become coarse, and consequently it may be difficult to achieve the effect of the present invention. The treatment temperature is most preferably a temperature of 1350-1750° C.

As a pressure medium in HIP treatment, argon gas is generally used. Gases other than argon, such as nitrogen and oxygen may be used.

In the composition and treatment condition of the present invention, since forming of anisotropic grains is initiated at a high temperature, densification is achieved without generating intragranular pores which inhibit translucency by densifying fine sintered grains in pressureless sintering. Furthermore, by promoting the growth of anisotropic grains characteristic of the sintered body of the present invention in the subsequent HIP treatment, an alumina sintered body having coloring with high aesthetic nature and high toughness while maintaining high translucency is obtained.

EXAMPLES

The present invention is specifically described below by Examples and Comparative Examples, but the invention is not limited to these Examples.

Evaluation methods of the sintered body of the present invention are described below.

(1) Fracture Toughness

A fracture toughness test was measured by SEPB method based on "Fracture toughness test method of fine ceramics" of JIS R1607. An average value of five measurements was adopted.

(2) Flexural Strength

A flexural test was measured by a three-point flexural test based on "Flexural strength test method of fine ceramics" of JIS R1601. An average value of ten measurements was adopted.

(3) Total Forward Transmittance

Total forward transmittance was measured by a double beam-system spectrophotometer (V-650 Model, manufactured by JASCO Corporation) based on "Test method of optical characteristics of plastics" of JIS K7105 and "Test method of total forward transmittance of plastics and transparent materials" of JIS K7361-1. A measurement sample used was a sample obtained by processing a sintered body to a thickness of 1 mm and mirror polishing both sides to a surface roughness Ra=0.02 μm or less. Light emitted from a light source (deuterium lamp and halogen lamp) was passed through a sample and scattered, and total forward transmission amount was measured using an integrating sphere. A measurement wavelength region was from 200-800 nm, and total forward transmittance in the present invention was the maximum value at a wavelength of 300-800 nm.

(4) Long Axis Length and Aspect Ratio of Grains, and Fraction of Anisotropic Grains A sintered body was mirror-polished, followed by chemical etching to emphasize grain boundaries and coat with gold thereon. It was observed using a scanning electron micrography or optical micrography, and values were calculated by image analysis of these photographs. Each grain approximated to rectangular, and a long side was measured as a long axis length, and a short side was measured as a short axis length. A value obtained by dividing the long axis length by the short axis length was adopted as an aspect ratio. Grains having a long axis length of 10 μm or greater, and an aspect ratio of 1.5 or more were selected, and volume fraction was calculated from the area occupied by these grains. The number of grains measured was 100 or more. Meanwhile, the chemical etching was conducted by immersing a sintered body in a supersaturated sodium borate solution at 80° C. to deposit it on a surface of the sintered body, heating at 900° C. for 0.5 hour, cooling, and washing using a hydrochloric acid solution.

(5) Density of Sintered Body

It was determined by measuring the weight of sintered body in water by Archimedes method. A relative density was calculated based on theoretical density of 3.98 g/cm$^3$.

Example 1

To a high purity alumina powder ($\alpha$-$Al_2O_3$: manufactured by TAIMEI CHEMICALS CO., LTD., 99.99% or more of purity), manganese oxide (MnO: manufactured by JAPAN PURE CHEMICAL CO., LTD., 99.9% purity), nickel oxide (NiO: manufactured by RARE METALLIC CO., LTD., 99.99% purity), copper oxide (CuO: manufactured by Wako Pure Chemical Industries, Ltd., 99.9% purity), vanadium oxide ($V_2O_5$: manufactured by Wako Pure Chemical Industries, Ltd., first grade reagent), iron oxide ($Fe_3O_4$, manufactured by KANTO CHEMICAL CO., INC., first grade reagent), and titanium oxide ($TiO_2$: manufactured by Kishida Chemical Co., Ltd., 99.5% purity) were added and mixed by ball-mill in ethanol. The resulting mixture was dried and used as a raw material powder.

The content of each of transition metal oxides was 500 ppm with respect to alumina. Impurities containing in the high purity alumina powder used as the raw material were shown in Table 1. The total amount of these oxides was 20 ppm or less. Meanwhile, impurities not shown in Table 1 were not greater than detection limit (<1 ppm).

Using a uniaxial press apparatus and a mold, pressure of 50 MPa was applied to powders having compositions shown in Table 2 to form plate-shaped molded articles having 40 mm×50 mm and a thickness of 5 mm. The molded articles were placed in a rubber mold, and pressure of 200 MPa was applied with a cold isostatic press apparatus to harden them. The resulting articles were sintered at 1300° C. for 2 hours in the air to obtain primary sintered bodies. The primary sintered bodies were treated at a temperature 1450-1650° C. under a pressure of 150 MPa for 1 hour in an argon gas medium by HIP apparatus. The fraction of anisotropic grains having a long axis length of 10 μm or greater and an aspect ratio of 1.5 or more, fracture toughness, flexural strength, and total forward transmittance of the resulting sintered bodies were determined. The results are shown in Table 2.

It was clear that translucent colored alumina sintered bodies having both high fracture toughness and high translucency were obtained.

TABLE 1

| $Na_2O$ (ppm) | $K_2O$ (ppm) | CaO (ppm) | $SiO_2$ (ppm) | Total (ppm) |
|---|---|---|---|---|
| 5 | 3 | 2 | 6 | 16 |

TABLE 2

| Sample No. | Transition metal 500 ppm | HIP Temp. (° C.) | Sintered body coloring | Fraction of anisotropic grains (vol %) | Fracture Toughness (MPa·m$^{0.5}$) | Flexural strength (MPa) | Total forward transmittance (%) | Sintered body density (%) |
|---|---|---|---|---|---|---|---|---|
| 1-1 | MnO | 1450 | Pink | 46.7 | 8.6 | 366 | 75.3 | 100 |
| 1-2 | CuO | 1450 | Brown | 59.9 | 6.5 | 483 | 60.2 | 100 |

TABLE 2-continued

| Sample No. | Transition metal 500 ppm | HIP Temp. (° C.) | Sintered body coloring | Fraction of anisotropic grains (vol %) | Fracture Toughness (MPa·m$^{0.5}$) | Flexural strength (MPa) | Total forward transmittance (%) | Sintered body density (%) |
|---|---|---|---|---|---|---|---|---|
| 1-3 | V$_2$O$_5$ | 1475 | Light yellow-green | 41.2 | 6.3 | 320 | 62.3 | 100 |
| 1-4 | Fe$_3$O$_4$ | 1500 | Light yellow | 21.8 | 5.1 | 580 | 77.8 | 100 |
| 1-5 | TiO$_2$ | 1500 | Light Yellow | 23.8 | 5.0 | 561 | 75.0 | 100 |
| 1-6 | NiO | 1650 | Green | 22.6 | 6.1 | 530 | 74.2 | 100 |

Example 2

To the high purity alumina powder described in Example 1, cobalt oxide (CoO: manufactured by RARE METALLIC Co., Ltd., 99.9% purity), chromium oxide (Cr$_2$O$_3$: manufactured by RARE METALLIC Co., Ltd., 99.99% purity), manganese oxide, vanadium oxide, nickel oxide and sodium metasilicate (Na$_2$O.SiO$_2$, manufactured by ALDRICH CORPORATION) were added and mixed by ball-mill in ethanol. The resulting mixture was dried and used as a raw material powder. The content of each transition metal oxide and sodium metasilicate was 500 ppm and 50 ppm with respect to alumina, respectively.

Sintered bodies were obtained by conducting the same treatment as Example 1 except for using powders having compositions shown in Table 3. The fraction of anisotropic grains having a long axis length of 10 μm or greater and an aspect ratio of 1.5 or more, fracture toughness, flexural strength, and total forward transmittance of the resulting sintered bodies were determined. The results are shown in Table 3.

It was clear that translucent colored alumina sintered bodies having both high fracture toughness and high translucency were obtained.

TABLE 3

| Sample No. | Transition metal 500 ppm | Sodium metasilicate | HIP Temp. (° C.) | Sintered body coloring | Fraction of anisotropic grains (vol %) | Fracture toughness (MPa·m$^{0.5}$) | Flexural strength (MPa) | Total forward transmittance (%) | Sintered body density (%) |
|---|---|---|---|---|---|---|---|---|---|
| 2-1 | CrO | 50 ppm | 1500 | Red-violet | 30.5 | 6.5 | 465 | 76.6 | 100 |
| 2-2 | Co$_2$O$_3$ | 50 ppm | 1600 | Blue | 25.3 | 5.8 | 538 | 68.9 | 100 |
| 2-3 | MnO | 50 ppm | 1450 | Pink | 50.6 | 7.0 | 349 | 72.3 | 100 |
| 2-4 | V$_2$O$_5$ | 50 ppm | 1475 | Light yellow-green | 42.3 | 6.6 | 315 | 61.3 | 100 |
| 2-5 | NiO | 50 ppm | 1650 | Green | 24.6 | 6.4 | 513 | 72.3 | 100 |

Comparative Example 1

Using chromium oxide and cobalt oxide which do not have a eutectic point with alumina together with the high purity alumina powder described in Example 1, sintered bodies were produced under the same condition as Example 1. The results of coloring, fracture toughness, flexural strength, and total forward transmittance (maximum value at sample thickness 1 mm, wavelengths 300-800 nm) of the resulting sintered bodies are shown in Table 4. In sintered bodies containing only transition metal oxides which do not have a eutectic point with alumina, anisotropic grains did not grow, and only sintered bodies having low toughness were obtained.

TABLE 4

| Sample No. | Transition metal 500 ppm | HIP Temperature (° C.) | Sintered body coloring | Fracture Toughness (MPa·m$^{0.5}$) | Flexural strength (MPa) | Total forward transmittance (%) | Sintered body Density (%) |
|---|---|---|---|---|---|---|---|
| 3-1 | CrO | 1500 | Red-violet | 3.3 | 701 | 73.2 | 100 |
| 3-2 | Co$_2$O$_3$ | 1600 | Blue | 4.2 | 598 | 62.2 | 100 |

While the invention has been described in detail and with reference to specific embodiments thereof, it will be apparent to one skilled in the art that various changes and modifications can be made therein without departing from the spirit and scope thereof.

This application is based on Japanese patent application filed on Nov. 18, 2008 (Application No. 2008-294498) and Japanese patent application filed on Nov. 18, 2008 (Application No. 2008-294499), the contents thereof being incorporated herein by reference.

INDUSTRIAL APPLICABILITY

The translucent colored alumina sintered body of the present invention has both high toughness and translucency, and thus it is very suitable for conventional ornament, jewelry and craftwork articles, as well as dental materials such as an orthodontic bracket and a mill blank for artificial denture which require high toughness not to break upon processing and coloring aesthetic nature for fashion. Therefore, this invention has a significant industrial value.

The invention claimed is:

1. An alumina sintered body, wherein the alumina sintered body
   contains at least one transition metal oxide,
   contains sintered grains,
   has a fracture toughness of 4.5 Mpa·m$^{0.5}$ or more, and
   has a total forward transmittance of 60% or more at a wavelength of light from 300 to 800 nm, wherein the total forward transmittance is measured with a sample having a thickness of 1 mm and
   wherein the sintered grains comprise anisotropic grains having a long axis length of 10 μm or greater and an aspect ratio of 1.5 or more.

2. The alumina sintered body as claimed in claim 1, wherein the alumina sintered body contains the transition metal oxide in the range of 100 ppm-3 wt % in total.

3. The alumina sintered body as claimed in claim 1, wherein the fraction of anisotropic grains having a long axis length of 10 μm or greater and an aspect ratio of 1.5 or more is 20 vol % or more.

4. The alumina sintered body as claimed in claim 1, wherein the transition metal oxide has a eutectic point with alumina.

5. The alumina sintered body as claimed in claim 4, wherein the transition metal oxide having a eutectic point with alumina is at least one oxide selected from the group consisting of manganese oxide, copper oxide, vanadium oxide, iron oxide, titanium oxide, and nickel oxide.

6. The alumina sintered body as claimed in claim 1, further containing at least one oxide selected from the group consisting of Group 1A alkali metal oxides, Group 2A alkaline earth metal oxides, and $SiO_2$, $B_2O_3$, $P_2O_5$ and $GeO_2$.

7. The alumina sintered body as claimed in claim 6, containing at least one oxide selected from the group consisting of Group 1A alkali metal oxides, Group 2A alkaline earth metal oxides, and $SiO_2$, $B_2O_3$, $P_2O_5$ and $GeO_2$ in the range of 20-1000 ppm.

8. A method for producing the alumina sintered body of claim 1, comprising molding an alumina powder containing at least one transition metal oxide in the range of 100 ppm-3 wt % in total, pressureless sintering the resulting molded article, and subjecting the resulting sintered body to a hot isostatic pressing (HIP) treatment.

9. The method for producing an alumina sintered body as claimed in claim 8, wherein the transition metal oxide is at least one transition metal oxide selected from the group consisting of manganese oxide, copper oxide, vanadium oxide, iron oxide, titanium oxide, and nickel oxide.

10. The method for producing an alumina sintered body as claimed in claim 8, wherein the alumina powder further contains at least one oxide selected from the group consisting of Group 1A alkali metal oxides, Group 2A alkaline earth metal oxides, and $SiO_2$, $B_2O_3$, $P_2O_5$ and $GeO_2$ in the range of 20-1000 ppm in total.

11. The method for producing an alumina sintered body as claimed in claim 8, wherein the alumina powder is a high purity alumina powder having a specific surface area of 5-20 m$^2$/g, and the fraction of 1 μm or smaller fine grains of 90 vol % or more.

12. The method for producing an alumina sintered body as claimed in claim 8, wherein the pressureless sintering is conducted at a temperature of 1250-1450° C.

13. The method for producing an alumina sintered body as claimed in claim 8, wherein the hot isostatic pressing (HIP) treatment is conducted at a temperature of 1350-1750° C. under a pressure of 50 MPa or more.

14. A dental material made from the alumina sintered body as claimed in any one of claims 1 to 7.

15. The dental material as claimed in claim 14, wherein the dental material is an orthodontic bracket or a mill blank for artificial denture.

* * * * *